US012611434B2

(12) United States Patent
Chen et al.

(10) Patent No.: US 12,611,434 B2
(45) Date of Patent: Apr. 28, 2026

(54) BIFIDOBACTERIUM BREVIS AND ITS APPLICATION IN PREVENTING OR ALLEVIATING PSORIASIS THEREOF

(71) Applicant: Jiangnan University, Wuxi (CN)

(72) Inventors: Wei Chen, Wuxi (CN); Wenwei Lu, Wuxi (CN); Yadan Deng, Wuxi (CN); Qixiao Zhai, Wuxi (CN); Bo Yang, Wuxi (CN); Shumao Cui, Wuxi (CN); Bingyong Mao, Wuxi (CN); Hongchao Wang, Wuxi (CN); Jianxin Zhao, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 337 days.

(21) Appl. No.: 18/212,253

(22) Filed: Jun. 21, 2023

(65) Prior Publication Data

US 2023/0346856 A1     Nov. 2, 2023

Related U.S. Application Data

(63) Continuation of application No. PCT/CN2021/117116, filed on Sep. 8, 2021.

(30) Foreign Application Priority Data

Dec. 24, 2020     (CN) .......................... 202011551202.7

(51) Int. Cl.
*A61K 35/745*     (2015.01)
*A23L 33/135*     (2016.01)
*A61P 17/06*     (2006.01)

(52) U.S. Cl.
CPC .......... *A61K 35/745* (2013.01); *A23L 33/135* (2016.08); *A61P 17/06* (2018.01)

(58) Field of Classification Search
None
See application file for complete search history.

(56) References Cited

U.S. PATENT DOCUMENTS

2022/0211776 A1* 7/2022 Yang ...................... A23L 33/40

FOREIGN PATENT DOCUMENTS

| CN | 112111424 A | 12/2020 |
| CN | 112546074 A | 3/2021 |
| WO | 2005000882 A2 | 1/2005 |

OTHER PUBLICATIONS

Fitch Erin et. al., "Pathophysiology of psoriasis: recent advances on IL-23 and Th17 cytokines", Current Rheumatology Reports vol. 9, Dec. 31, 2007, 1-13p. 461-467.
Cesare A.D. et. al., "The IL-23/Th17 Axis in the Immunopathogenesis of Psoriasis", Journal of Investigative Dermatology vol. 129, (Mar. 26, 2009), 1-13P1339-1350.
Vergou T. et. al. , "Targeting the IL-12/IL-23 cytokine family in the treatment of psoriatic disease", Expert Rev. Dermatol. vol. 3, No. 4 (Dec. 31, 2008), 1-13.P453-463.

* cited by examiner

*Primary Examiner* — Brian Gangle
(74) *Attorney, Agent, or Firm* — IPro, PLLC; Na Xu

(57) ABSTRACT

The disclosure discloses a strain of *Bifidobacterium breve* capable of preventing and relieving psoriasis and application thereof, belonging to the field of microbial technologies and medical technologies. The disclosure provides new uses of *B. breve* CCFM1078 in inhibiting the release of IL-23/Th17 axis related inflammatory factors, and relieving the psoriasis. The *B. breve* CCFM1078 of the disclosure can relieve the lesion skin of psoriasis-like mice, and can inhibit thickening of the skin epidermal layer, so that the IL-23 level, the IL-22 level and the IL-17 level in the skin decrease by 20.3%, 22.0% and 18.3%, respectively. The *B. breve* CCFM1078 has a great application prospect in the preparation of a product (such as a food, a drug or a health food) for preventing and/or treating psoriasis.

14 Claims, 3 Drawing Sheets

1

BIFIDOBACTERIUM BREVIS AND ITS APPLICATION IN PREVENTING OR ALLEVIATING PSORIASIS THEREOF

TECHNICAL FIELD

The disclosure relates to a strain of *Bifidobacterium breve* capable of preventing and relieving psoriasis and application thereof, belonging to the field of microbial technologies and medical technologies.

BACKGROUND

T helper cell 17 (Th17) is a newly discovered T cell subpopulation that can secrete interleukin-17 (IL-17), and has important significance in autoimmune diseases and body defense reaction. After receiving antigen stimulation, a naive CD4$^+$T cell can differentiate into different subtypes of T cells under different conditions and perform different functions. The differentiation direction of the naive CD4$^+$T cell is regulated by many factors such as the nature of an antigen, hormones and cytokines in a local environment, where the types of the cytokines and the balance between the cytokines play an important role in regulating the differentiation of Th cells. IL-23 belongs to an IL-12 family member and is a heterodimer, including an IL-23 specific p19 subunit and an IL-12 shared p40 subunit. An IL-23 receptor is also a heterodimer correspondingly, which is composed of two subunits: IL-12Rβ1 and IL-23R. The IL-23R is mainly expressed in a T cell, a natural killer T cell, a monocyte and a dendritic cell. The IL-23 plays an important role in the differentiation of Th17 cells and can directly induce a primitive T cell to produce IL-22 and IL-17. The IL-23/Th17 axis is involved in the occurrence of various diseases, including psoriasis, arthritis, inflammatory bowel disease, etc.

The psoriasis is a chronic, genetically and environmentally co-induced, immune-mediated inflammatory disease, which is non-infectious and prone to recurrence, and may gradually worsen with age, or its severity is up and down, and even some cases suffer from life-long devastating consequences. The global prevalence rate of the psoriasis published by the World Health Organization in 2016 was 0.09% to 11.43%. In China, the prevalence rate of the psoriasis is less than 0.5%. The prevalence rate of the psoriasis appears to be higher in high-latitude countries, which may be related to different UV intensities caused by different latitudes. The psoriasis is more likely to occur in adults than in children. Although the psoriasis can occur at any age, the highest incidence rate is between 18 and 39 years old or 50 and 69 years old. The pathogenesis of the psoriasis is not yet totally clear. The increase of proinflammatory cytokine released by immune related cells and the chronic activation of innate and adaptive immune systems are considered to be mechanisms that lead to long-term damage to multiple tissues and organs. Currently, various psoriasis related abnormalities have been reported, including antigen presentation and the activation of an NF-κB signaling pathway, the differentiation of a T helper cell population (especially a TH17 cell, the main source of the IL-17) and the enhancement of the IL-17 reaction. These abnormalities promote the immune response of a host and the infiltration of immune cells. Liu Aimin, Qiao Ju, Guo Qinghao, et al. have reported an increase in the expression levels of the IL-23, the IL-22 and the IL-17 in the serum of psoriasis patients.

There is currently no medical method or drug for completely curing the psoriasis, which remains a global medical problem. The treatment method for the psoriasis depends on several factors. In the early stage, local treatment is often used. A lesion region determines the formula and dosage of the local treatment. Corticosteroids are the main method for the local treatment of the psoriasis at present. When a conventional treatment regimen has poor efficacy, a biological agent can be considered for use. In recent years, various high-efficiency biological agents can be used for treating moderate to severe psoriasis, mainly including a tumor necrosis factor (TNF) inhibitor, a T cell modulator, an IL-12/23p40 inhibitor and an IL-17A inhibitor. the importance of the IL-23 and the IL-17 has been emphasized in research in recent years, and thus, the research focus places emphasis on biological agents for the IL-23 and the IL-17. But the biological agents are expensive.

Probiotics are a type of active microorganisms that are beneficial to the host and change the composition of flora of a certain part of the host by colonization in a human body. Short-chain fatty acids, metabolites of the probiotics, are important mediators connecting the host and intestinal flora, and have a biological effect. For example, butyric acid can promote Treg cell differentiation, thereby influencing the Th17/Treg balance and reducing the IL-17 levels. Related foreign research also confirmed this possibility. Chen et al. intervened psoriasis-like mice with *Lactobacillus pentosus* GMNL-77. The results showed that the *L. pentosus* reduced the levels of the IL-23, the IL-22 and the IL-17 in the skin of the mice, and the conditions of the mice were alleviated. David et al. found that after 26 psoriasis patients received continuous oral administration of *Bifidobacterium infantis* 35624 for 6 weeks, their conditions were relieved.

Therefore, the current situations that the psoriasis is difficult to treat and prone to recurrence, and side effects are big may be addressed by developing the probiotics that can inhibit the release of the IL-23/Th17 axis related inflammatory factors.

SUMMARY

The disclosure provides new uses of *B. breve* CCFM1078 or a product containing the *B. breve* CCFM1078 in inhibiting the release of IL-23/Th17 axis related inflammatory factors, preventing and/or relieving psoriasis. The *B. breve* CCFM1078 was deposited in the Guangdong Microbiological Culture Collection Center on May 6, 2020, with the preservation number of GDMCC No. 61011, and the preservation address is 5$^{th}$ floor, Building 59, Compound 100, Xianlie Middle Road, Guangzhou city.

In an embodiment, the relieving psoriasis includes at least one use of (a) or (b):

(a) Effectively improving skin folds, scales and/or erythema;

(b) Inhibiting skin cuticle thickening.

In an embodiment, the inhibiting release of IL-23/Th17 axis related inflammatory factors specifically involves reducing the IL-23 level, the IL-22 level and the IL-17 level in the skin of a psoriasis-like individual.

In an embodiment, the product includes a food, a drug, or a health food.

In an embodiment, the viable count of the *B. breve* CCFM1078 in the product is not less than 1×10$^6$ CFU/mL or 1×10$^6$ CFU/g.

In an embodiment, the drug contains the *B. breve* CCFM1078, a drug carrier and/or a pharmaceutical adjuvant.

In an embodiment, the drug carrier includes microcapsules, microspheres, nanoparticles and liposomes.

In an embodiment, the pharmaceutical adjuvant includes an excipient and an additive.

In an embodiment, the pharmaceutical adjuvant includes an anti-adhesive agent, a penetration enhancer, a buffer agent, a plasticizer, a surfactant, an antifoaming agent, a thickener, an inclusion agent, an absorbent, a humectant, a solvent, a propellant, a solubilizer, a cosolvent, an emulsifier, a colorant, a pH value regulator, an adhesive, a disintegrant, a filler, a lubricant, a wetting agent, an integrating agent, an osmotic pressure regulator, a stabilizer, a flow aid, a corrigent, a preservative, a foaming agent, a suspending agent, a coating material, an aromatic, a diluent, a flocculant and a decoagulant agent, a filter aid and a release blocker.

In an embodiment, the additive includes microcrystalline cellulose, hydroxypropylmethylcellulose and refined lecithin.

In an embodiment, the drug includes the dosage forms of granules, capsules, tablets, pills, or oral liquid.

In an embodiment, the food is a food containing the B. breve CCFM1078 or fermentation metabolites thereof.

In an embodiment, the food is a dairy product, bean product, fruit and vegetable product produced by using the B. breve CCFM1078 or a fermentation agent containing the B. breve CCFM1078.

In an embodiment, the food is a solid beverage containing the B. breve CCFM1078.

In an embodiment, a preparation method of the fermentation agent is as follows: inoculating the B. breve CCFM1078 into a medium with an inoculum size accounting for 2 to 4% of the total mass of the medium, performing culture at 37° C. for 30 h to obtain a culture solution; centrifuging the culture solution and collecting bacterial cells; washing the bacterial cells with a phosphate buffer solution with pH of 7.2 for 3 times, and then performing resuspension with a freeze-drying protective agent to obtain a resuspension solution; freeze-drying the resuspension solution by a vacuum freezing method to obtain the fermentation agent of the B. breve CCFM1078.

In an embodiment, a mass ratio of the freeze-drying protective agent to the bacterial cells is 2:1.

In an embodiment, the freeze-drying protective agent contains skimmed milk powder, maltodextrin and L-sodium glutamate, where skimmed milk powder:Maltodextrin:L-sodium glutamate=(8-10):(8-10):1.

In an embodiment, the medium is prepared by dissolving skimmed milk, glucose, tryptone and yeast extract, accounting for 10%, 0.5%, 1.5% and 0.3% of the total mass of the medium respectively, in water.

In an embodiment, the medium has the pH of 6.8.

Beneficial Effects: The disclosure provides a strain of B. breve CCFM1078 that inhibits the release of IL-23/Th17 axis related inflammatory factors, thereby preventing and/or relieving psoriasis. When the B. breve CCFM1078 is used in the psoriasis-like mice, the following effects can be achieved:

The skin conditions of the psoriasis-like mice are improved;

Thickening of the skin epidermal layer of the psoriasis-like mice is inhibited;

The IL-23 level in the skin of the psoriasis-like mice decreases by 20.3%;

The IL-22 level in the skin of the psoriasis-like mice decreases by 22.0%; and

The IL-17 level in the skin of the psoriasis-like mice decreases by 18.3%.

Therefore, the B. breve CCFM1078 has a great application prospect in the preparation of the product (such as the food, the drug or the health food) for preventing and/or relieving psoriasis.

Biological Material Preservation

The B. breve CCFM1078 was deposited in the Guangdong Microbiological Culture Collection Center on May 6, 2020, with the preservation number of GDMCC No. 61011, and the preservation address is 5th floor, Building 59, Compound 100, Xianlie Middle Road, Guangzhou city.

DETAILED DESCRIPTION

Figure 1:
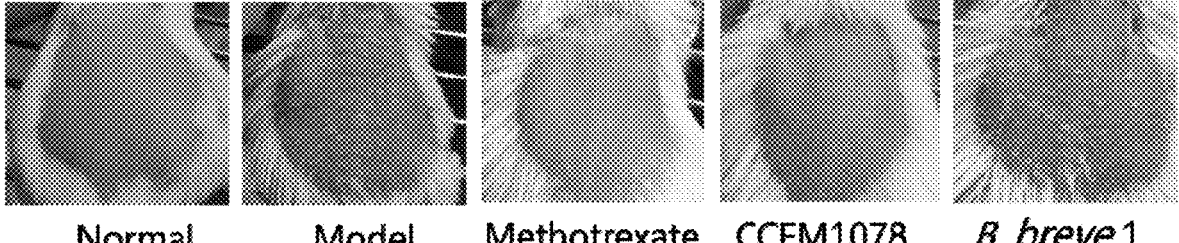
FIG. 1: Lesion skin conditions of experimental mice of different groups.

Media involved in the following examples are as follows:

mMRS medium formula (1 L): peptone 10 g, beef extract 10 g, yeast powder 5 g, glucose 20 g, $K_2HPO_4$ 2 g, diammonium citrate 2 g, sodium acetate 2 g, Tween 80 1 mL, $MgSO_4 \cdot 7H_2O$ 0.5 g, cysteine hydrochloride 0.5 g and $MnSO_4 \cdot 4H_2O$ 0.25 g, with pH of 7.2 to 7.4.

mMRS solid medium formula (1 L): peptone 10 g, beef extract 10 g, yeast powder 5 g, glucose 20 g, $K_2HPO_4$ 2 g, diammonium citrate 2 g, sodium acetate 2 g, Tween 80 1 mL, $MgSO_4 \cdot 7H_2O$ 0.5 g, cysteine hydrochloride 0.5 g, $MnSO_4 \cdot 4H_2O$ 0.25 g and agar 20 g, with pH of 7.2 to 7.4.

Detection methods involved in the following examples are as follows:

Viable count detection method: the national standard "GB 4789.35-2016 National Food Safety Standard, Food Microbiological Detection: Lactic Acid Bacteria Detection" is employed.

Acidity detection method: the national standard GB 431334-2010 is employed.

B. breve 1 is another strain isolated from a different fecal sample by employing the same method.

Example 1: Culture of B. breve

After B. breve CCFM1078 was inoculated in the mMRS solid medium and cultured at 37° C. for 48 h, colonies of the B. breve was observed and bacterial cells of the B. breve was observed under a microscope. It was found that the colony of the B. breve is milky white, irregular, round, bulged and smooth, and the bacterial cell is Campylobacter jejuni with slightly irregular and round ends, and usually exists in single, paired, and small clusters.

After B. breve CCFM1078 was inoculated in an MRS liquid medium and cultured at 37° C. for 30 h, the B. breve CCFM1078 was transferred into a fresh MRS liquid medium and cultured for 30 h under the same condition. Bacterial cells were centrifuged 6000×g for 15 min. The bacterial cells were washed with 0.9% physiological saline, and then centrifuged at 6000×g again for 10 min. The bacterial cells were collected, and resuspended with a 30% (m/v) sucrose solution, and the resuspended bacterial cells were cryopreserved at 80° C. for later use.

The *B. breve* 1 was prepared into a bacterial solution by employing the same method as described above.

Example 2: Relieving Effect of *B. breve* on Lesion Skin of Mice with Psoriasis 6 to 8-week-old SPF-class BALB/c female mice were divided into 4 groups: a normal group, a model group, a positive reference group (hereinafter referred to as PRG) and experimental groups. drug methotrexate was used in PRG. The experimental groups included a CCFM1078 group intragastrically administrated with the *B. breve* CCFM1078 and a *B. breve* 1 group intragastrically administrated with the *B. breve* 1, with 6 animals in each group. All mice were raised in the Experimental Animal Center of Jiangnan University and fed with ordinary feed, at a constant temperature of 21 to 26° C. and at the humidity of 40 to 70%, with noise of less than or equal to 60 dB, and animal illumination of 15 to 20 LX (all animal experiment procedures were reviewed and approved by the Animal welfare and Ethics Management Committee of Jiangnan University).

The experimental cycle was a total of 3 weeks, and modeling was performed in week 3. The back of the mice was depilated the day before modeling, in an area of about 2.5 cm×2.5 cm. During the modeling, imiquimod cream was applied daily to the ears and back depilated regions of the mice in the model group and experimental group, 10 mg for the ears and 62.5 mg for the back, and only the same amount of petroleum jelly was applied to the normal group. During the experiment, the methotrexate group was intragastrically administered with 1 mg/kg/day of methotrexate solution (the methotrexate solution was a solution prepared by dissolving methotrexate in sterile physiological saline). During the modeling, the CCFM1078 group was intragastrically administered daily with 0.2 mL of CCFM1078 bacterial suspension (prepared according to the method in Example 1) with the viable count of $1\times10^9$ CFU/mL. The *B. breve* 1 group was intragastrically administered daily with 0.2 mL of *B. breve* 1 bacterial suspension (prepared according to the method in Example 1) with the viable count of $1\times10^9$ CFU/mL. The normal group and the model group were only intragastrically administered with an equal amount of sterile physiological saline as a control. All the groups were given free drinking water and food intake. During the modeling, the back of the mice was photographed and recorded daily, and the mice were sacrificed on the $1^{st}$ day of week 4. The results are shown in FIG. 1.

From FIG. 1, it could be seen that the skin in the back depilated region of the mice in the normal group is smooth, without scales or erythema, while the skin in the back depilated region of the mice in the model group has a fold feeling, is covered with obvious scales accompanied by erythema. Compared with the model group, the CCFM1078 group has smooth skin in the back depilated region, and substantially no scales or erythema, which is similar to the skin condition of the methotrexate group, while the skin in the back depilated region of the mice in the *B. breve* 1 group, like that of the model group, has a fold feeling and was covered with obvious scales.

The above experimental results showed that compared with the *B. breve* 1, the *B. breve* CCFM1078 can more effectively relieve symptoms of skin lesions in the mice with psoriasis.

Example 3: Inhibition Effect of *B. breve* on Cuticle Thickening of Mice with Psoriasis 6 to 8-week-old SPF-class BALB/c female mice were divided into 4 groups: a normal group, a model group, a positive reference group (hereinafter referred to as PRG) and experimental groups, where the experimental groups included a CCFM1078 group intragastrically administrated with the *B. breve* CCFM1078 and a *B. breve* 1 group intragastrically administrated with the *B. breve* 1, with 6 animals in each group. All mice were raised in the Experimental Animal Center of Jiangnan University and fed with ordinary feed, at a constant temperature of 21 to 26° C. and at the humidity of 40 to 70%, with noise of less than or equal to 60 dB, and animal illumination of 15 to 20 LX (all animal experiment procedures were reviewed and approved by the Animal welfare and Ethics Management Committee of Jiangnan University).

The experimental cycle was a total of 3 weeks, and modeling was performed in week 3. The back of the mice was depilated the day before modeling, in an area of about 2.5 cm×2.5 cm. During the modeling, imiquimod cream was applied daily to the ears and back depilated regions of the mice in the model group and experimental group, 10 mg for the ears and 62.5 mg for the back, and only the same amount of petroleum jelly was applied to the normal group. In weeks 1 to 3, during the experiment, the CCFM1078 group was intragastrically administered daily with 0.2 mL of CCFM1078 bacterial suspension (prepared according to the method in Example 1) with the viable count of $1\times10^9$ CFU/mL. The *B. breve* 1 group was intragastrically administered daily with 0.2 mL of *B. breve* 1 bacterial suspension (prepared according to the method in Example 1) with the viable count of $1\times10^9$ CFU/mL. The methotrexate group was intragastrically administered with 1 mg/kg/day of methotrexate solution (the methotrexate solution was a solution prepared by dissolving methotrexate in sterile physiological saline). The normal group and the model group were only intragastrically administered with an equal amount of sterile physiological saline as a control. All the groups were given free drinking water and food intake. The mice were sacrificed on the 1st day of week 4, and a part of the skin from the back depilated region of the mice was taken for making a pathological section for histopathological analysis. The results are shown in FIG. 2.

Figure 2:
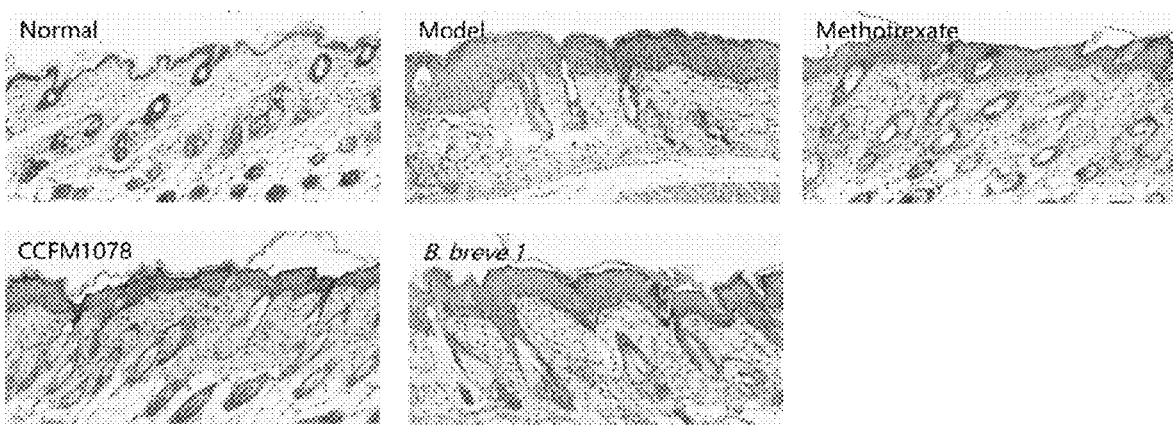
FIG. 2: Skin pathological sections of experimental mice of different groups.

From FIG. 2, it could be seen that the skin epidermal layer of the mice in the blank group is only composed of one or two layers of cells, and there is no inflammatory reaction in each layer of the epidermis, while the mice in the model group shows significant cuticle thickening accompanied by severe inflammation. Compared with the model group, the CCFM1078 group shows no significant cuticle thickening and mild inflammation, which is substantially similar to the skin condition of the methotrexate group, while the mice in the *B. breve* 1 group shows significant skin cuticle thickening and severe inflammation.

The above experimental results showed that compared with the *B. breve* 1, the *B. breve* CCFM1078 can more effectively inhibit cuticle thickening of the lesion skin of the mice with psoriasis.

Example 4: Influence of *B. breve* on IL-23 in Skin of Mice with Psoriasis 6 to 8-week-old SPF-class BALB/c female mice were divided into 4 groups: a normal group, a model group, a positive reference group (hereinafter referred to as PRG) and experimental groups, where the experimental groups included a CCFM1078 group intragastrically administered with the *B. breve* CCFM1078 and a *B. breve* 1 group intragastrically administered with the *B. breve* 1, with 6 animals in each group. All mice were raised in the Experimental Animal Center of Jiangnan University and fed with ordinary feed, at a constant temperature of 21 to 26° C. and at the humidity of 40 to 70%, with noise of less than or equal to 60 dB, and animal illumination of 15 to 20 LX (all animal experiment procedures were reviewed and approved by the Animal welfare and Ethics Management Committee of Jiangnan University).

The experimental cycle was a total of 3 weeks, and modeling was performed in week 3. The back of the mice was depilated the day before modeling, in an area of about 2.5 cm×2.5 cm. During the modeling, imiquimod cream was applied daily to the ears and back depilated regions of the mice in the model group and experimental group, 10 mg for the ears and 62.5 mg for the back, and only the same amount of petroleum jelly was applied to the normal group. During the experiment, the CCFM1078 group was intragastrically administered daily with 0.2 mL of CCFM1078 bacterial suspension with the viable count of $1\times10^9$ CFU/mL. The *B. breve* 1 group was intragastrically administered daily with 0.2 mL of *B. breve* 1 bacterial suspension with the viable count of $1\times10^9$ CFU/mL. The methotrexate group was intragastrically administered with 1 mg/kg/day of methotrexate solution (the methotrexate solution was a solution prepared by dissolving methotrexate in sterile physiological saline). The normal group and the model group were only intragastrically administered with an equal amount of sterile physiological saline as a control. All the groups were given free drinking water and food intake. The mice were sacrificed on the 1st day of week 4, a part of the skin of the back depilated region of mice was taken and stored at −80° C., and the content of IL-23 in the skin was detected by an ELISA kit. The results are shown in FIG. 3.

Figure 3:
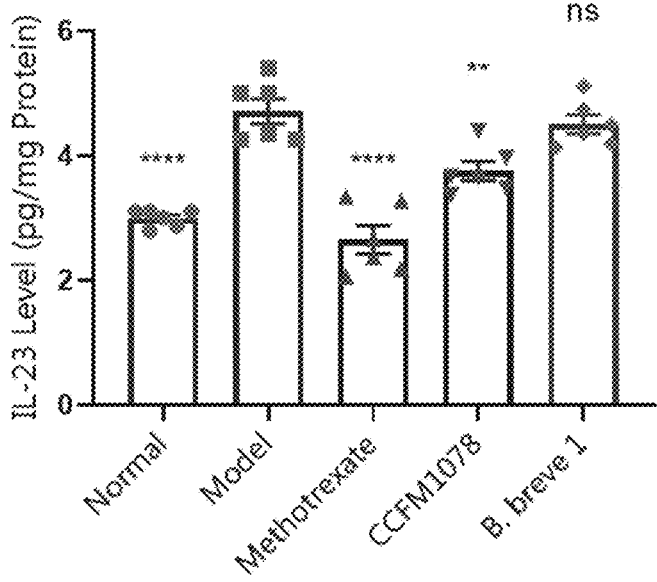
FIG. 3: IL-23 content in the skin of experimental mice of different groups.

From FIG. 3, it could be seen that after the mice are intragastrically administered with the *B. breve* CCFM1078, the content of the IL-23 in the skin decreases by 20.3%, which is significantly lower than that of the model group ($p<0.01$), indicating that although the inhibition effect of the strain in the disclosure is not as good as that of the drug methotrexate (the IL-23 level decreases by 43.8% compared with that of the model group, and even the IL-23 level is lower than that of the blank group), the strain can indeed inhibit the inflammatory reaction, while after the mice are intragastrically administered with the *B. breve*', the content of the IL-23 in the skin only decreases by 4.4%, which is not significantly different from that of the model group.

The above experimental results showed that the *B. breve* CCFM1078 can significantly down-regulate typical upregulation pro-inflammatory factors in the mice with psoriasis to a normal level, especially reducing the IL-23 level, which is significantly superior to that of another strain of *B. breve* 1.

Example 5: Influence of *B. breve* on IL-22 in Skin of Mice with Psoriasis 6 to 8-week-old SPF-class BALB/c female mice were divided into 4 groups: a normal group, a model group, a positive reference group (hereinafter referred to as PRG) and experimental groups, where the experimental groups included a CCFM1078 group intragastrically administrated with the *B. breve* CCFM1078 and a *B. breve* 1 group intragastrically administrated with the *B. breve* 1, with 6 animals in each group. All mice were raised in the Experimental Animal Center of Jiangnan University and fed with ordinary feed, at a constant temperature of 21 to 26° C. and at the humidity of 40 to 70%, with noise of less than or equal to 60 dB, and animal illumination of 15 to 20 LX (all animal experiment procedures were reviewed and approved by the Animal welfare and Ethics Management Committee of Jiangnan University).

The experimental cycle was a total of 3 weeks, and modeling was performed in week 3. The back of the mice was depilated the day before modeling, in an area of about 2.5 cm×2.5 cm. During the modeling, imiquimod cream was applied daily to the ears and back depilated regions of the mice in the model group and experimental group, 10 mg for the ears and 62.5 mg for the back, and only the same amount of petroleum jelly was applied to the normal group. During the experiment, the CCFM1078 group was intragastrically administered daily with 0.2 mL of CCFM1078 bacterial suspension with the viable count of $1\times10^9$ CFU/mL. The *B. breve* 1 group was intragastrically administered daily with 0.2 mL of *B. breve* 1 bacterial suspension with the viable count of $1\times10^9$ CFU/mL. The methotrexate group was intragastrically administered with 1 mg/kg/day of methotrexate solution (the methotrexate solution was a solution prepared by dissolving methotrexate in sterile physiological saline). The normal group and the model group were only intragastrically administered with an equal amount of sterile physiological saline as a control. All the groups were given free drinking water and food intake. The mice were sacrificed on the 1st day of week 4, a part of the skin of the back depilated region of mice was taken and stored at −80° C., and the content of IL-22 in the skin was detected by an ELISA kit. The results are shown in FIG. 4.

Figure 4:
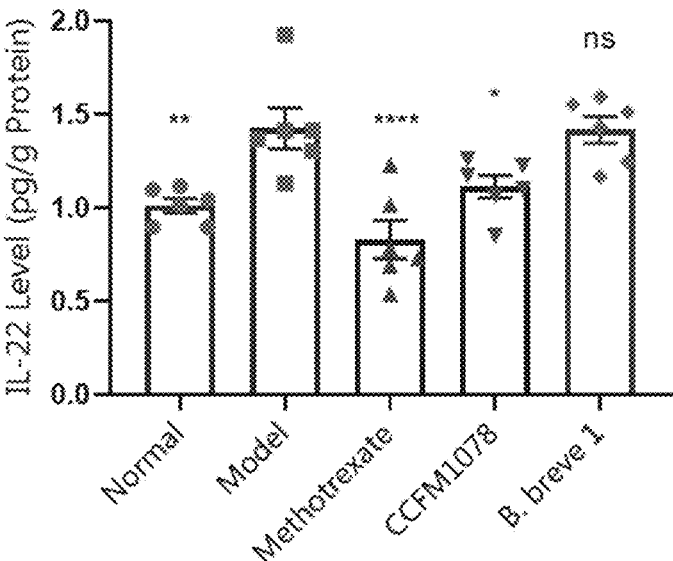
FIG. 4: IL-22 content in the skin of experimental mice of different groups.

From FIG. 4, it could be seen that after the mice are intragastrically administrated with the *B. breve* CCFM1078, the content of the IL-22 in the skin decreased by 22.0%, which is significantly lower than that of the model group ($p<0.05$), indicating that although the inhibition effect of the strain in the disclosure is not as good as that of the drug methotrexate (the IL-22 level decreases by 41.8% compared with that of the model group, and even the IL-22 level is lower than that of the blank group), the strain can indeed inhibit the inflammatory reaction, while after the mice are intragastrically administrated with the *B. breve* 1, the content of the IL-22 in the skin only decreases by 0.5%, which is not significantly different from that of the model group.

The above experimental results showed that the *B. breve* CCFM1078 can significantly down-regulate typical upregulation pro-inflammatory factors in the mice with psoriasis to a normal level, especially reducing the IL-22 level, which is significantly superior to that of another strain of *B. breve* 1.

Example 6: Influence of *B. breve* on IL-17 in Skin of Mice with Psoriasis 6 to 8-week-old SPF-class BALB/c female mice were divided into 4 groups: a normal group, a model group, a positive reference group (hereinafter referred to as PRG) and experimental groups, where the experimental groups included a CCFM1078 group intragastrically administrated with the *B. breve* CCFM1078 and a *B. breve* 1 group intragastrically administrated with the *B. breve* 1, with 6 animals in each group. All mice were raised in the Experimental Animal Center of Jiangnan University and fed with ordinary feed, at a constant temperature of 21 to 26° C. and at the humidity of 40 to 70%, with noise of less than or equal to 60 dB, and animal illumination of 15 to 20 LX (all animal experiment procedures were reviewed and approved by the Animal welfare and Ethics Management Committee of Jiangnan University).

The experimental cycle was a total of 3 weeks, and modeling was performed in week 3. The back of the mice was depilated the day before modeling, in an area of about 2.5 cm×2.5 cm. During the modeling, imiquimod cream was applied daily to the ears and back depilated regions of the mice in the model group and experimental group, 10 mg for the ears and 62.5 mg for the back, and only the same amount of petroleum jelly was applied to the normal group. During the experiment, the CCFM1078 group was intragastrically administered daily with 0.2 mL of CCFM1078 bacterial suspension with the viable count of $1 \times 10^9$ CFU/mL. The *B. breve* 1 group was intragastrically administered daily with 0.2 mL of *B. breve* 1 bacterial suspension with the viable count of $1 \times 10^9$ CFU/mL. The normal group and the model group were only intragastrically administered with an equal amount of sterile physiological saline as a control. All the groups were given free drinking water and food intake. The mice were sacrificed on the 1st day of week 4, a part of the skin of the back depilated region of mice was taken and stored at −80° C., and the content of IL-17 in the skin was detected by an ELISA kit. The results are shown in FIG. 5.

Figure 5:
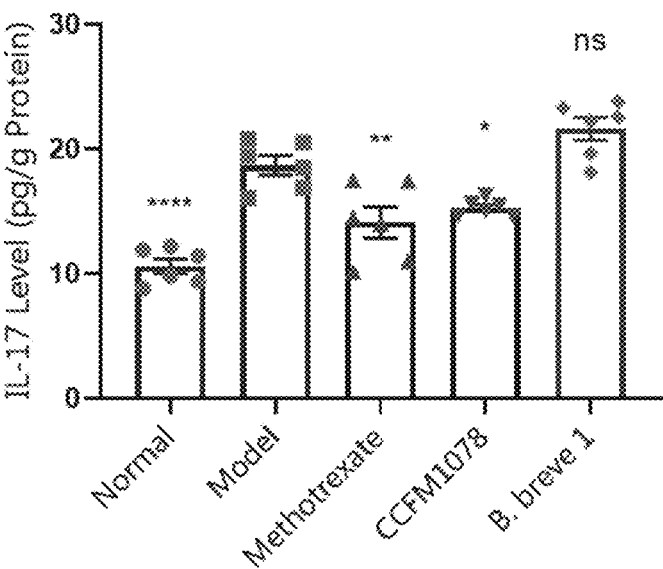
FIG. 5: IL-17 content in the skin of experimental mice of different groups.

From FIG. 5, it could be seen that after the mice are intragastrically administrated with the *B. breve* CCFM1078, the content of the IL-17 in the skin decreases by 18.3%, which is significantly lower than that of the model group (p<0.05), indicating that although the inhibition effect of the strain in the disclosure is not as good as that of the drug methotrexate (the IL-17 level decreases by 24.6% compared with that of the model group), the strain can indeed inhibit the inflammatory reaction, while after the mice are intragastrically administrated with the *B. breve* 1, the content of IL-17 in the skin even increases.

The above experimental results showed that the *B. breve* CCFM1078 can significantly down-regulate typical upregulation pro-inflammatory factors in the mice with psoriasis to a normal level, especially reducing the IL-17 level, which is significantly superior to that of another strain of *B. breve* 1.

Example 7: Preparation of Bacterial Powder Containing *B. breve* CCFM1078

A seed solution of the *B. breve* CCFM1078 was inoculated into the mMRS medium with an inoculation amount accounting for 3% of the total mass of the medium, culture was performed at 37° C. for 30 h to obtain a culture solution; the culture solution was centrifuged and bacterial cells were collected; the bacterial cells were washed with a phosphate buffer solution with pH of 7.2 for 3 times, and then resuspension was performed with a trehalose freeze-drying protective agent with a trehalose concentration of 100 g/L, and a mass ratio of the freeze-drying protective agent to the bacterial cell was controlled to be 2:1 to obtain a resuspension solution; and the resuspension solution was immediately transferred to a freeze-drying machine for drying for 24 h after being pre-cooled for 1.5 h at −80° C. to obtain *B. breve* CCFM1078 bacterial powder.

Example 8: Preparation of Yogurt Containing *B. breve* CCFM1078

Milk powder, inulin, *stevia* sugar and water were mixed in a weight ratio of 20:5:5:75 and homogenized to prepare a fermentation raw material; ultra-high temperature sterilization was performed at 121° C. for 300 s, and then the sterilized fermentation raw material was cooled to 42° C.; the mixed bacterial powder of *Lactobacillus bulgaricus* and *Streptococcus thermophilus* was inoculated for fermentation at 42° C. for 12 h, and then, the cell concentration of the *L. bulgaricus* and the cell concentration of the *S. thermophilus* were controlled to be $10^5$ CFU/g and $10^7$ CFU/g, respectively, and then blending was performed; a fermented product was cooled to 37° C., the freeze-dried bacterial powder of the *B. breve* CCFM1078 was added. The feed amount of the freeze-dried bacterial powder of the *B. breve* CCFM1078 was $10^9$ CFU *breve* CCFM1078 per ml of yogurt; the mixture was stirred, jarred, and stored at 4° C. for 2 days for natural postripeness prepare probiotic yogurt.

Example 9: Comparison Between *B. breve* CCFM1078 and *B. infantis* 35624

David et al. found that after 26 psoriasis patients received continuous oral administration of *B. infantis* 35624 for 6 weeks, their conditions were relieved. Specifically, the levels of C-reactive protein, IL-6, and TNF-α in the serum of a patient with psoriasis decreases, while the skin lesion of the patient are not described. The *B. breve* CCFM1078 reduces the level of Th17/IL-23 axis related inflammatory factors, specifically IL-23, IL-22 and IL-17, in skin lesion part of the psoriasis-like mice, which is different from a site targeted by the *B. infantis* 35624. Moreover, the *B. breve* CCFM1078 has a significant inhibition effect on cuticle thickening of the skin lesion part of the psoriasis-like mice, and effectively improves the erythema and scale symptoms of the skin lesion. Therefore, the relieving effect of the *B. breve* CCFM1078 on psoriasis is different from that of the *B. infantis* 35624.

Although the disclosure has been disclosed with preferred examples, it is not intended to limit the disclosure. Anyone familiar with this technology, without departing from the spirit and scope of the disclosure, can make various changes and modifications. Therefore, the scope of protection of the disclosure should be based on the scope defined in Claims.

What is claimed is:

1. A method for preventing and/or relieving psoriasis in a subject in need thereof, which comprises:
administering to the subject *Bifidobacterium breve* CCFM1078 or a product comprising the *B. breve* CCFM1078, such that the *B. breve* CCFM1078 is ingested into the subject's stomach and intestines,
wherein the *B. breve* CCFM1078 was deposited in the Guangdong Microbiological Culture Collection Center on May 6, 2020, with the preservation number of GDMCC No. 61011.

2. The method according to claim 1, wherein the relieving psoriasis in the subject comprises at least one of (a) or (b):
(a) effectively improving skin folds, scales, and/or erythema in the subject;
(b) inhibiting skin cuticle thickening in the subject.

3. The method according to claim 1, wherein administering the *B. breve* CCFM1078 to the subject inhibits release of IL-23/Th17 axis-related inflammatory factors, and wherein inhibiting the release of the IL-23/Th17 axis-related inflammatory factors comprises reducing levels of IL-23, IL-22, and IL-17 in the skin of the subject.

4. The method according to claim 1, wherein the product comprises a food or a drug.

5. The method according to claim 1, wherein a viable count of the *B. breve* CCFM1078 administered to the subject is not less than $1 \times 10^6$ CFU/mL or $1 \times 10^6$ CFU/g.

6. The method according to claim 4, wherein the product is the drug, and wherein the drug further comprises a drug carrier and/or a pharmaceutical adjuvant.

7. The method according to claim 6, wherein the drug carrier is one or more selected from the group consisting of: microcapsules, microspheres, nanoparticles, and liposomes; and wherein the pharmaceutical adjuvant comprises an excipient or an additive.

8. The method according to claim 7, wherein the additive comprises one or more of: microcrystalline cellulose, hydroxypropylmethylcellulose, and refined lecithin.

9. The method according to claim 6, wherein a dosage form of the drug is granules, capsules, tablets, pills, or oral liquid.

10. The method according to claim 4, wherein the product is the food, and wherein the food further comprises a fermentation metabolite of the *B. breve* CCFM1078.

11. The method according to claim 4, wherein the food is one or more of a dairy product, bean product, fruit product, or vegetable product.

12. The method according to claim 10, wherein the food is a beverage.

13. The method according to claim 1, wherein the product is a fermentation agent, and wherein the fermentation agent is prepared according to the following method:

inoculating the *B. breve* CCFM1078 into a medium, incubating the medium at 35° C. to 37° C. for 20 hours to 30 hours to obtain a culture solution;

centrifuging the culture solution and collecting bacterial cells;

washing the bacterial cells, resuspending with a freeze-drying protective agent to obtain a resuspension solution; and freeze-drying the resuspension solution to obtain the fermentation agent of the *B. breve* CCFM1078.

14. A method for preventing and/or relieving psoriasis in a subject in need thereof, which comprises:

administering to the subject *Bifidobacterium breve* CCFM1078 or a product comprising the *B. breve* CCFM1078, such that the *B. breve* CCFM1078 is ingested into the subject's stomach and intestines, wherein the *B. breve* CCFM1078 was deposited in the Guangdong Microbiological Culture Collection Center on May 6, 2020, with the preservation number of GDMCC No. 61011, wherein the product is a drug comprising a drug carrier and/or a pharmaceutical adjuvant, wherein the drug carrier is one or more selected from the group consisting of: microcapsules, microspheres, nanoparticles, and liposomes, wherein the pharmaceutical adjuvant comprises an excipient or an additive, and wherein the additive comprises one or more of: microcrystalline cellulose, hydroxypropylmethylcellulose, and refined lecithin.

\* \* \* \* \*